United States Patent [19]

Bellas

[11] Patent Number: 5,186,180
[45] Date of Patent: Feb. 16, 1993

[54] INTRA-VAGINAL PROLAPSE DIAGNOSTIC INSTRUMENT

[76] Inventor: Gabriel A. S. Bellas, Qta. mary, 4ta transversal, Urbanización Horizonte, El Marques, Caracas, Venezuela

[21] Appl. No.: 705,790

[22] Filed: May 28, 1991

Related U.S. Application Data

[63] Continuation-in-part of Ser. No. 390,189, Aug. 7, 1989, abandoned.

[51] Int. Cl.⁵ .............................................. A61B 5/103
[52] U.S. Cl. ........................................ 128/778; 33/512
[58] Field of Search ..................... 128/772, 774, 778; 606/1; 33/511, 512, 836

[56] References Cited

U.S. PATENT DOCUMENTS

| | | | |
|---|---|---|---|
| 3,478,435 | 11/1969 | Cook | 33/511 |
| 4,121,572 | 10/1978 | Krzeminski | 33/836 X |
| 4,362,167 | 12/1982 | Nicolai et al. | 128/778 |
| 4,685,474 | 8/1987 | Kurz et al. | 128/778 |
| 4,760,847 | 8/1988 | Vaillancourt | 33/512 X |
| 5,010,892 | 4/1991 | Colvin et al. | 128/774 |
| 5,013,318 | 5/1991 | Spanta, III | 33/512 X |
| 5,034,009 | 7/1991 | Mouchel | 128/778 X |
| 5,109,869 | 5/1992 | Buckley | 128/778 |

FOREIGN PATENT DOCUMENTS

| | | | |
|---|---|---|---|
| 2622428 | 5/1989 | France | 128/778 |
| 0730355 | 4/1978 | U.S.S.R. | 128/778 |

*Primary Examiner*—Kyle L. Howell
*Assistant Examiner*—Krista M. Pfaffle
*Attorney, Agent, or Firm*—Dennison, Meserole, Pollack & Scheiner

[57] ABSTRACT

This invention is related to an instrument for detecting prolapse in early stages, consists of a three principal parts: an elongated cylindrical rigid plunger with an annular notch, a tubular body with a concave flange and a scale tube where measurement can be taken. This instrument is placed intra-vaginally and its measuring scale is a basis for a diagnosis.

5 Claims, 2 Drawing Sheets

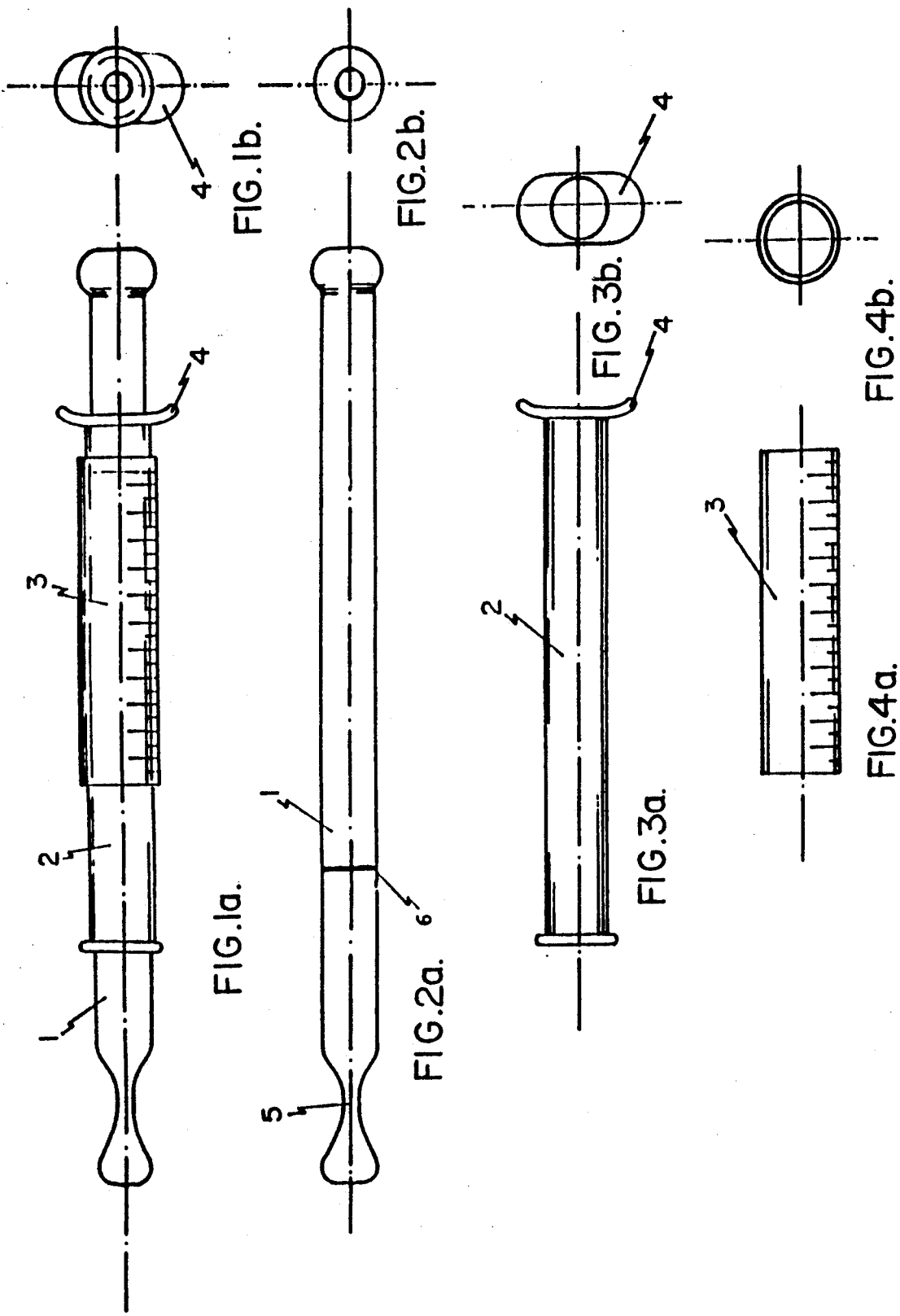

I

INTRA-VAGINAL PROLAPSE DIAGNOSTIC INSTRUMENT

RELATED U.S. APPLICATION DATA

This application is a continuation-in-part of U.S. Ser. No. 07/390,189, filed Aug. 7 1989, and now abandoned.

FIELD OF THE INVENTION

This invention in general is related to the field of gynecological instruments and in particular it refers to an intra-vaginal instrument for measuring prolapse in women that have had sexual intercourse and are not pregnant.

BACKGROUND OF THE INVENTION

The woman uterus in normal anteversoflexion position is supported by round ligaments to the fundus and its abdominal wall, and by the utero-sacral ligaments to the sacrum. Utero-sacral ligaments determine the position of the cervix. Parametrium ligaments form two fan shape structures which are laterally positioned and fix the uterine cervix and the vaginal vault to the pelvis. Paravaginal ligaments are also laterally positioned and passively hold upper third part of the vagina and actively hold the lower two thirds. Any lesion to this system causes a drop of the uterus and the vagina, which is called prolapse.

The prolapse of the uterus and in its absence of the vaginal vault, what is called utero-vaginal prolapse, have three clinical phases: TYPE I, in which the drop is slight without reaching the vaginal introitus; TYPE II, in which the drop is pronounced and the uterus enters the vaginal introitus; and TYPE III, in which the drop is total and the uterus is out of the external genitals. TYPE II and III prolapses are easily diagnosed, however TYPE I, is difficult to discover and usually goes undetected.

There are no prior art intra-vaginal instruments for measuring a utero-vaginal prolapse. The only prior art instruments pertinent to this area are the instruments adapted for dimensional measurement of uterine and pelvimetrical cavity. The following U.S. patents disclose developments in this field: U.S. Pat. No. 4,121,572 Krzeminski and U.S. Pat. No. 4,685,474 Kurz et al. Both instruments are created to be introduced inside the uterus, through the cervix to obtain one (Krzeminski) or two (Kurz et al.) internal measurements of the uterus cavity. The Krzeminski's and the present invention are both gynecological measuring instruments, so both have measuring scales, although located in different parts. The principal difference is a functional construction adapted to the specific purpose for which they served. Krzeminski's invention consists of two principal parts: a probe with measuring indicia and a horseshoe-shaped body. According to Krzeminski's invention an uterine sound is introduced into the uterus for a measurement of its depth. The distal end of this sound is no more than 2-3 mm, to be able to pass through the cervical os. The measurement is taken by moving the sound only in one direction into the uterus. The most important parts of Krzeminski's invention are the internal stop elements which allow to avoid any displacement and to maintain the precise measurement, once the sound is taken out of the uterus. No measurement different than the depth of the uterine cavity can be taken with this instrument. It cannot be simply placed into the uterus without additional help of other gynecological instruments. First the vagina must be opened by a speculum and than a clamp must be used to enter a spherically-shaped nub of the sound's probe into the cervical os. Such operation needs antiseptic means, is invasive and painful and can even require anaesthesia. The measurement is taken by the examiner without the woman's active participation. The Kurz et al., invention's objective is similar to the Krzeminski's but it is more complex, because two measurements of the uterus can be taken, depth and width.

The present invention is an intra-vaginal prolapse diagnostic instrument only, which cannot be introduced into the uterus, because the plunger which is placed into the vagina is too wide, as it has minimum diameter of 1.5 cm. The measurement is taken in a totally different way, from Krzeminski and Kurz. The present invention consists of three principal parts all of which must be set on a common point, before the measurement can be performed. In the case of the Krzeminski invention a probe is simply pressed ahead into the uterus by the examiner and the resistance of the uterus wall determines the measurement. The present invention however, is to be placed into the vagina first, set in the common point and afterwards the woman is asked to strain. Such action expels the plunger indicating on the outer scale a precise measurement. The plunger moves outside the woman's body, exactly in the opposite direction to the Krzeminski's uterine sound. The present invention does not have any stop elements, and all its parts are concentric and are slidable without any friction in both directions. It can be placed into the vagina without use of any gynecological instruments, without antiseptic measures and without anaesthesia, as this instrument is not an invasive one, and does not cause any pain during the examination. The examiner needs however an active participation of the woman on whom the examination is performed.

Other pertinent prior art patents are U.S. Pat. No. 4,362,167 Nicolai, for measurement of the pelvimetrical cavity, which measures the internal traverse interischial spinous diameter of pelvis of pregnant women as an indication of whether vaginal or cesarean delivery should be performed and the U.S. Pat. No. 3,478,435 Cook, for measuring the thickness of animal tissues, which is an invasive and traumatic instrument adapted to be introduced through skin, fat and muscle implying a blind penetration through different tissues of the animal's body with probable lesions of blood vessels and nerves in any anatomic region excluding natural cavities such as vagina and uterus and its objective is to define an animal's corporal weight.

There are as well methods to detect utero-vaginal prolapse, however they imply x-ray cystograms, x-ray vaginograms and x-ray rectograms which are expensive, time consuming and can have side effects by exposing a woman's body to different x-ray radiations.

The present invention is inspired by the anatomical experiment performed in 1935 by William Mengert, who applied cuts and cross-sections of the different ligamental pairs of support of the uterus in several cadavers of women without prolapse, using a clamp adapted to the cervix of the uterus, a pulley and a ruler, and obtained measurements in centimeters of the displacements that occured when each supporting ligament was cut. These experiments laid the anatomical basis for the significance of measuring and quantifying in centimeters each support ligament of the uterus and the vagina. There is a direct and proportional relation between utero-vaginal ligamentary sufficiency. The objective of this invention is to provide an instrument for easy and rapid diagnosis of prolapse. The principal objective is to detect prolapse in its early stage of TYPE I, which generally is not detected with present techniques. The instrument is also useful for post-operatory follow up to determine the success of surgical techniques in cases where the surgery was performed.

BRIEF DESCRIPTION OF DRAWINGS

FIG. 1A - Lateral view of the instrument.

FIG. 1B - Front view of the instrument.

FIG. 2A - Lateral view of the cylindrical plunger with an annular notch.

FIG. 2B - Front view of the cylindrical plunger with an annular notch.

FIG. 3A - Lateral view of the transparent tubular body.

FIG. 3B - Front view of the transparent tubular body.

FIG. 4A - Lateral view of the transparent scale.

FIG. 4B - Front view of the transparent scale.

DESCRIPTION OF THE PREFERRED EMBODIMENT

Figure 6:
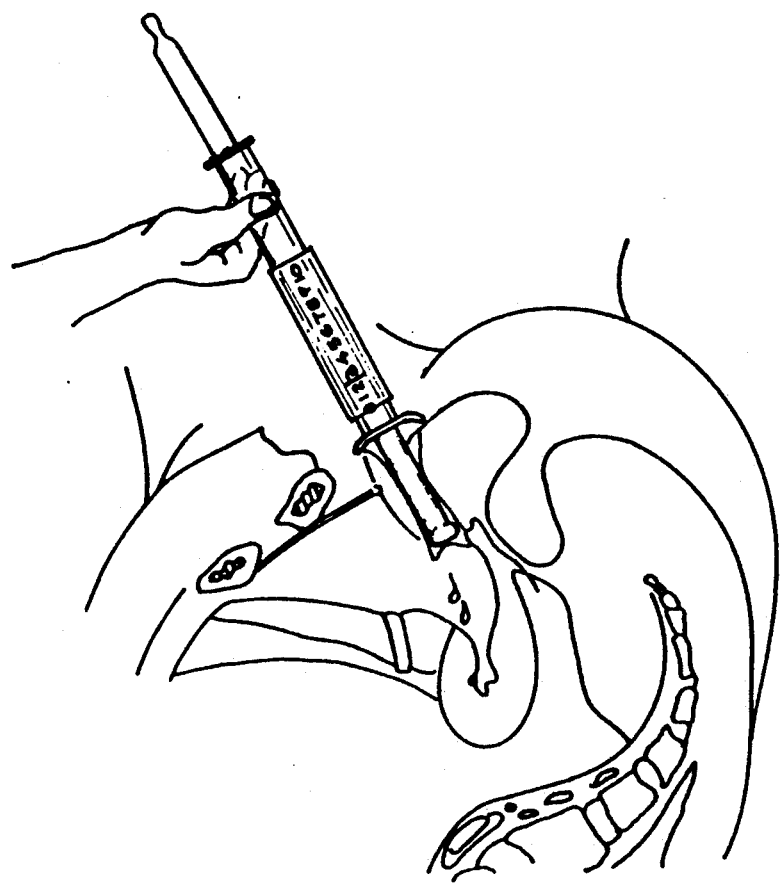
FIG. 6 - Anatomical cross-section with the instrument at a second position, placed within the vagina displaying the measurement.
Figure 5:
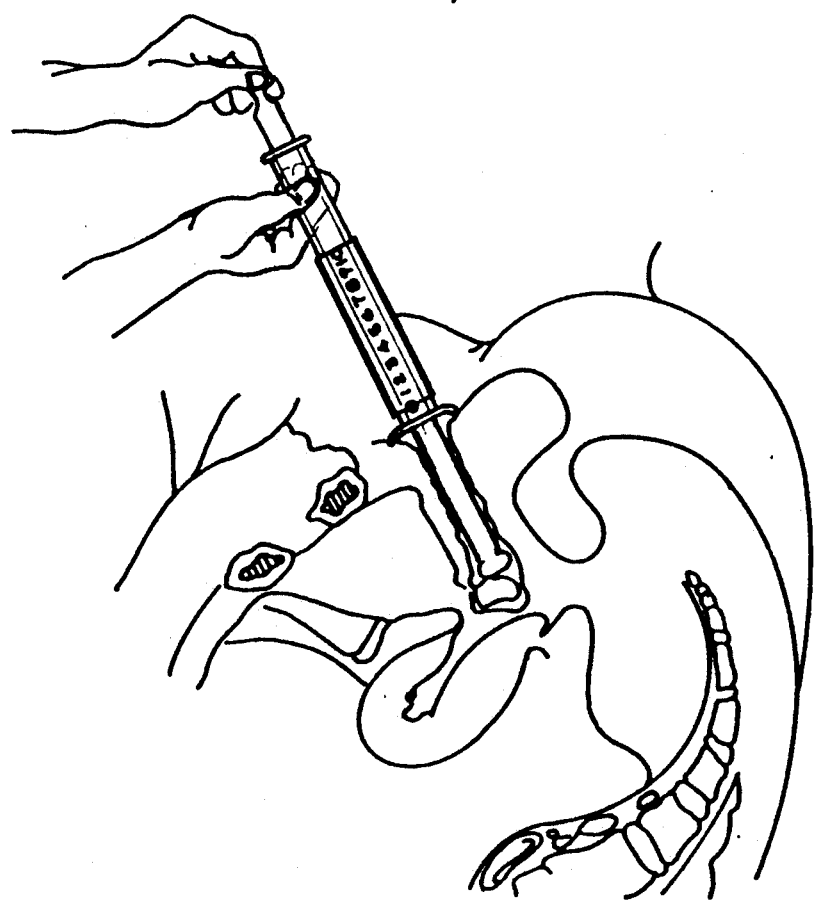
FIG. 5 - Anatomical cross-section with the instrument at a first position, placed within the vagina and adjusted to zero.

FIG. 1 shows a general view of the instrument comprised of an elongated cylindrical rigid plunger (1), which slides within a shorter transparent tubular body (2), which in turn slides within a shorter transparent scale tube (3) which has a measuring indicia scribed on it's whole length, and which is at least eight centimeters long. The plunger (1) has its ends semi-closed, so the air can pass freely inside. Its distal end has a bulbous shape, to be placed into the vagina, and its proximal end has a pinched portions for manual operation. It also has an annular notch (6) located at least twelve centimeters from its distal end. The reason for it is, that the notch has to be always outside the vagina, and as the vaginal length average is between 8-10 centimeters, the plunger's (1) length of 12 centimeters assures such condition. The tubular body (2) is transparent and has a distal end provided with a concave flange (4) to be placed in contact with the vagina's entrance during the examination, and has a thin annular flange on its proximal end. Both flanges are limiting a movement of the scale tube which slides freely between each other. The longest part of the instrument is a cylindrical plunger (1), followed by a tubular body (2), which represents approximately half of its length. The shortest part is a scale tube (3), which represents approximately half of the tubular body (2). Holding the instrument on the tubular body (2) with one hand, and operating the pinched portion with the other, the bulbous part of the plunger is pushed and slid into the vagina until its distal end comes up to the cervix of the uterus or to the vaginal vault of the histerectomized women. The concave flange of the tubular body (2) is pushed ahead to be in a direct contact with the vagina's entrance. In such a position, the instrument is set to coincide the zero on the scale tube (3) with the annular notch (6) on the plunger (1), which is possible due to the fact that both, the tubular body, as well as the scale tube are transparent. Once the instrument has been adjusted, the examined woman is asked to strain, this way expelling the plunger (1) through the tubular body (2). The plunger's movement can be measured through a movement of the notch. The quantity of centimeters between zero and the displaced notch gives the desired measurement, which is normally repeated and the greatest measurement is taken into account. FIGS. 2, 3 and 4 show separate elements of the present instrument. FIG. 5 and 6 show the instrument before and after examination.

Other variations not contemplated herein may be attempted, provided that they shall be circumscribed to the field and the scope of the idea herein described.

What is claimed is:

1. An intra-vaginal diagnostic instrument for detecting utero-vaginal prolapse comprising an elongated cylindrical plunger including a distal end and a proximal end, means defining an annular notch on said plunger, said distal end of said plunger including a bulbous terminal, and said proximal end including a pinched zone of diminished diameter, a tubular body encircling said plunger and including a distal end and a proximal end, said distal end of said tubular body terminating in a generally concave flange configured to engage the entrance of the vagina, an annular flange positioned on the proximal end of said tubular body, a scale tube mounted on the exterior of said tubular body for sliding movement thereon between said annular flange and said concave flange, measuring indicia on said scale tube configured to cooperate with said annular notch on said plunger to provide an indication of the depth of penetration of the bulbous end portion of said plunger into the vagina when said plunger is moved thereinto relative to said tubular body and said annular notch on said plunger is positioned beneath said measuring indicia on said scale tube.

2. The intra-vaginal prolapse diagnostic instrument as in claim 1, wherein said annular notch is located on said cylindrical plunger at least twelve centimeters from its distal end.

3. The intra-vaginal prolapse diagnostic instrument as in claim 1, wherein a cross-section diameter of said cylindrical plunger is between 1.5 and 2.5 centimeters.

4. The intra-vaginal prolapse diagnostic instrument as in claim 1, wherein said scale tube has a scale of at least eight centimeters.

5. The intra-vaginal prolapse diagnostic instrument as in claim 1, wherein said tubular body and said scale tube are transparent.

* * * * *